United States Patent [19]

Kakumoto et al.

[11] Patent Number: 4,841,443
[45] Date of Patent: Jun. 20, 1989

[54] METHOD OF AND APPARATUS FOR AUTOMATICALLY READING 5 BAND ARRAYAL PATTERN

[75] Inventors: Shigeru Kakumoto, Kodaira; Tatsuo Sumi; Tetsuo Kurisu, bothof Yokohama, all of Japan

[73] Assignees: Hitachi, Ltd.; Hitachi Software Engineering Co., Ltd., both of Tokyo, Japan

[21] Appl. No.: 924,788

[22] Filed: Oct. 30, 1986

[30] Foreign Application Priority Data

Oct. 30, 1985 [JP] Japan .............................. 60-241548
Oct. 30, 1985 [JP] Japan .............................. 60-241549

[51] Int. Cl.$^4$ .......................... G06K 9/00; G06K 9/12
[52] U.S. Cl. ........................... 364/413.01; 364/413.15; 382/6
[58] Field of Search ............. 364/413, 413.01, 413.15; 382/6; 435/6; 935/77

[56] References Cited

U.S. PATENT DOCUMENTS 3,932,839  3/1973  Stephens ................................. 382/6
4,706,192  11/1987  Nasu et al. ......................... 364/413

Primary Examiner—Jerry Smith
Assistant Examiner—Kim Thanh Tbui
Attorney, Agent, or Firm—Antonelli, Terry & Wands

[57] ABSTRACT

A pattern having a plurality of bands in each of a plurality of lanes is photoelectrically converted, and the sum (histogram) of the density data (pixel data) of pixels lying in lines, each of which passes through a plurality of points in a direction perpendicular to the lanes, is detected on the basis of the density data of the respective pixels photoelectrically converted. Points representative of the existence regions of the respective lanes, for example the central positions of the respective lanes, are detected from the histogram, and the density data items of the pixels in the detected central positions of the respective lanes are collected to obtain the spectra of the respective lanes. The spectra are used to detect the plurality of maximum positions of each of them as band positions, whereby the band positions are automatically read.

15 Claims, 11 Drawing Sheets

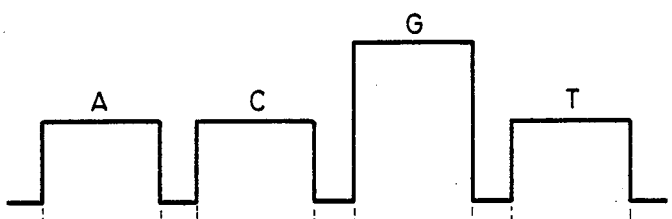
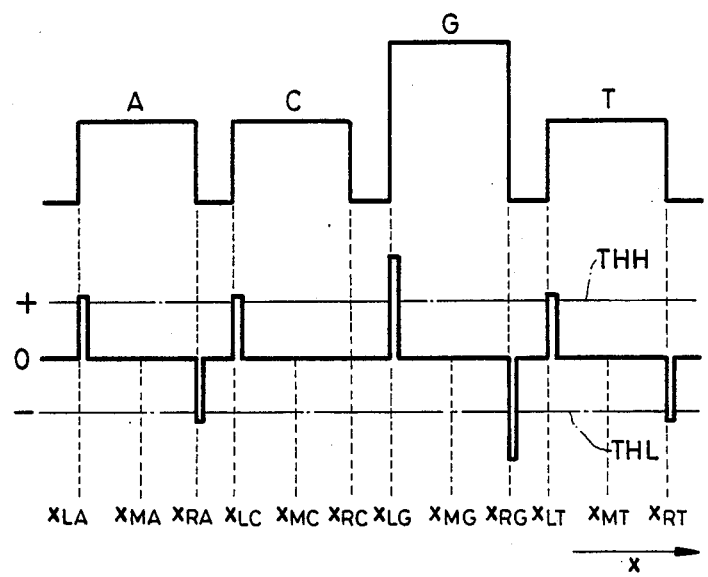
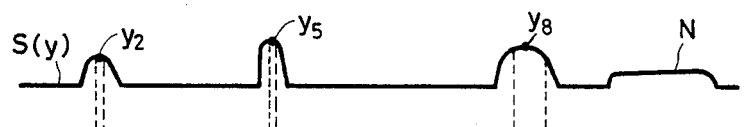
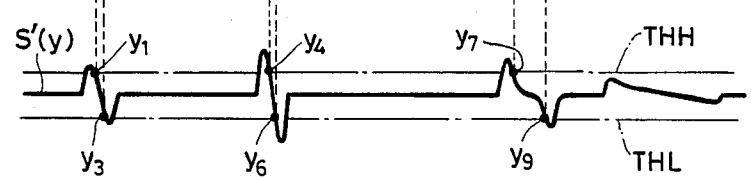
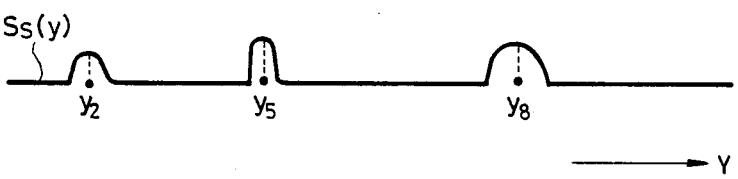

FIG. 6D
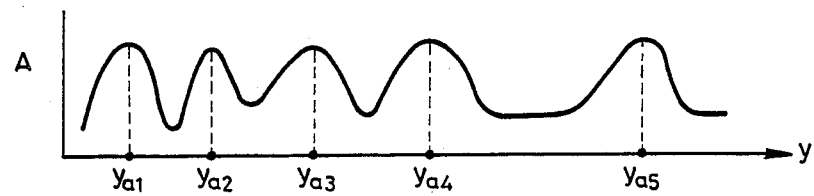
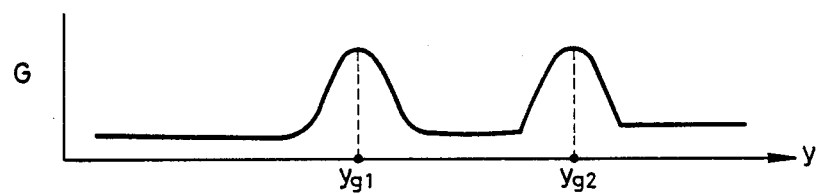
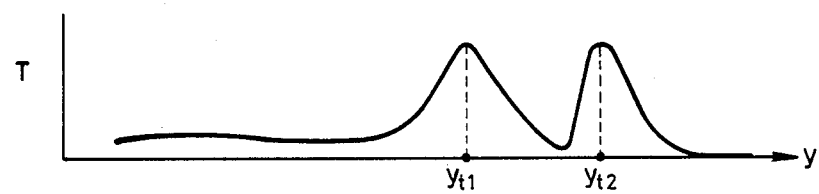
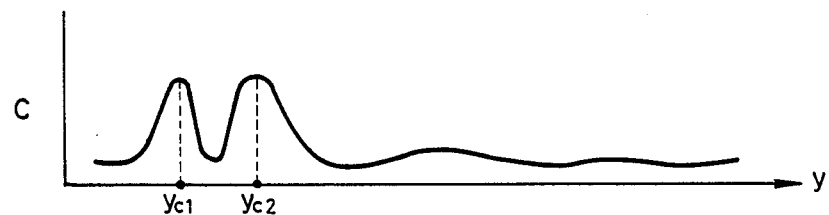
FIG. 6E
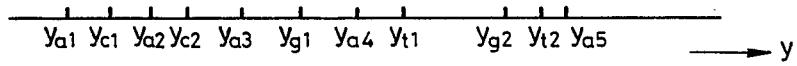

METHOD OF AND APPARATUS FOR AUTOMATICALLY READING 5 BAND ARRAYAL PATTERN

BACKGROUND OF THE INVENTION

The present invention relates to a method of and an apparatus for automatically reading a band arrayal pattern, and more particularly to a band arrayal pattern-automatic reading method and apparatus which are well suited to read the base band arrayal pattern of a gene imaged on an X-ray film and to correctly detect the band arrayal order of base codes.

It has been made clear and is generally known that the gene of a living organism is composed of the substance deoxyribonucleic acid (DNA) and has a structure in which the four kinds of organic bases; adenine (A), cytosine (C), guanine (G) and thymine (T) are arrayed in a double-helical shape. A method of determining the base arrayal of the DNA is the shotgun method. With this method, the chain of the DNA is broken up by reagents for chemically cutting the respective bases, and the individual bases are arrayed in accordance with their different lengths by electrophoresis, whereupon they are imaged on a film with X-rays. The X-ray film obtained after the electrophoresis bears belt-like patterns expressive of the arrayal of the four kinds of bases. As shown in FIG. 2A, on the film 3 subjected to the X-ray imaging, a plurality of bands 4 extending substantially perpendicularly to a lane are arrayed within the lane which is the valid range of each of the base codes A, C, G and T. The gene can be analyzed by analyzing the base arrayal on this film.

For the purpose of the analysis, the base arrayal pattern on the film is input to a computer. As an input device therefor, there has heretofore been one employing a digitizer in which the X-ray film 3 is placed on the digitizer, and the positions of the bands 4 on the film 3 are successively pointed to with a pen or cursor so as to input the output signals of the digitizer to the computer.

With the prior-art device, since the bands on the X-ray film are input by successively pointing to them by means of the pen or the like, it expends labor to input all the bands on the X-ray film. When the input operation is conducted for a long time, input mistakes increase.

Besides, a method of determining the base arrayal of the DNA has been disclosed in the official gazette of Japanese Patent Application Laid-open No. 59-126247, in which band positions are automatically read with a laser, and with reference to respective separation development positions having appeared in the separation development series of a mixture, the separation development positions of scission decomposition products unique to bases having appeared in another separation development series are compared for identification.

Another prior-art method of determining the base arrayal of the DNA has been disclosed in the official gazette of Japanese Patent Application Laid-open No. 59-44648, in which controls are put on both the sides of a sample so as to judge whether or not a band exists.

These prior art methods involve various restrictions in practical use.

SUMMARY OF THE INVENTION

An object of the present invention is to provide a method of and an apparatus for automatically reading band positions more easily.

In the present invention, a pattern having a plurality of bands in each of a plurality of lanes is photoelectrically converted, the sum (histogram) of the density data (pixel data) of pixels lying on lines each of which passes through a plurality of points in a direction perpendicular to the lanes is detected on the basis of the density data of the respective pixels photoelectrically converted, points representative of the existence regions of the respective lanes, for example the central positions of the respective lanes, are detected from the histogram, the density data items of the pixels on the detected central positions of the respective lanes are collected to obtain the spectra of the respective lanes, and the spectra are used to detect the plurality of maximum positions of each of them s band positions.

Thus, lane positions are accurately found, so that band representative positions, for example central positions can be accurately found.

In an especially preferable aspect of the performance of the present invention, the histogram in the direction perpendicular to the lanes is obtained every minute section in the extending direction of the lanes, and the positions of the representative points of the lane regions, for example the central positions of the lanes, are found for each of such sections. Thus, even in a case where the lanes are not always rectilinear, namely, where the lanes are meandering, the band positions can be accurately found.

In another aspect of the performance of the present invention, the positions of the central points of the lanes and the points of both the ends of the lanes are found as points representative of the lane regions, spectra in the extending direction of the lanes are obtained for the respective positions found, and the spectra are analyzed, thereby to find the central position and both end positions of respective bands. Thus, even when the bands are slanted to the lane direction, the band positions can be correctly detected.

Further, according to the present invention, an apparatus well-suited to perform the method of the present invention comprises a first memory which has storage locations corresponding to different positions in a direction perpendicular to lanes, a second memory in which pixel data items obtained by photoelectric conversion are stored in correspondence with the two-dimensional positions of the respective pixels of a pattern, means to add each pixel data on a single line of the pattern perpendicular to the lanes and the data of the corresponding position perpendicular to the lanes already written in said first memory and to write the result said first memory, again in synchronism with the photoelectric conversion of the pixel on the single line, so as to form histogram data for the respective positions perpendicular to the lanes, and means to detect a position of a point representative of an existence region of each lane on the basis of the histogram of said first memory, to read out of said second memory the pixel data items corresponding to the pixels on a line passing the detected point so as to obtain spectral data for each lane, and to detect a maximum position of the spectral data as a band position of each lane.

Thus, the band positions in the plurality of lanes on the pattern can be detected at high speed.

Further, in an aspect of the performance of the present invention, the addition means obtains the histogram every predetermined section in the extending direction of the lanes. In this case, the second memory consists of two areas for storing the pixel data items within two such sections, and in obtaining the histogram for a new section, the two areas are successively exchanged and used.

Thus, the second memory need not store all the pixel data items on the pattern but may store the pixel data items every fixed section, so that the apparatus is simplified.

In another aspect of the performance of the present invention, the positions of bands arrayed and forming lanes adjacent to each other are detected for the respective lanes, each of the detected band positions is normalized to a position on a single line in the lengthwise direction of the lane in accordance with the slope of the individual band, and the arrayal order of the bands is thereafter read.

Thus, even when the bands detected for the respective lanes are slanted with different slopes, the arrayal order of the bands can be correctly detected.

In another aspect of the performance of the present invention, the positions of bands arrayed and forming lanes adjacent to each other are detected for the respective lanes, and each of the detected band position is normalized to a position on a single line in the lengthwise direction of the lane in accordance with the slope of the individual band. The band interval of bands adjoining each other on the single line is compared with the smallest band interval as predetermined and a reference band interval depending upon a position on the single line, and the band is erased or re-detected.

Thus, the misreading of the band positions can be prevented.

BRIEF EXPLANATION OF THE DRAWINGS

FIGS. 4A-4F are diagrams for explaining the operation of the circuit in FIG. 1C, in which:

FIG. 4A is a time chart of read pixel data;

FIG. 4B is a time chart of an address counter 38;

FIG. 4C is a time chart of a "write strobe" for an addition memory 47 and an image memory 40;

FIG. 4D is a time chart of latch pulses for a latch circuit 45;

FIG. 4E is a time chart of the output of the latch circuit 45; and

FIG. 4F is a time chart of the output of an adder 44.

FIGS. 5A and 5B are diagrams for explaining a method of detecting the representative points of lane positions according to the apparatus of FIG. 1A, in which:

FIG. 5A shows histograms in the X-axial direction of lanes; and

FIG. 5B shows the differentiated waveforms of the histograms in FIG. 5A.

FIGS. 6A-6E are diagrams for explaining a method of detecting band positions within lanes according to the apparatus of FIG. 1A, in which:

FIG. 6A shows spectra in the Y-axial direction of the lanes;

FIG. 6B shows the differentiated waveforms of the spectra in FIG. 6A;

FIG. 6C shows analytical spectra which express the band positions;

FIG. 6D shows an example of analytical spectra obtained for respective bases; and FIG. 6E shows an example of detected base data corresponding to FIG. 6D.

DETAILED DESCRIPTION OF THE PREFERRED EMBODIMENTS

Figure 1A:
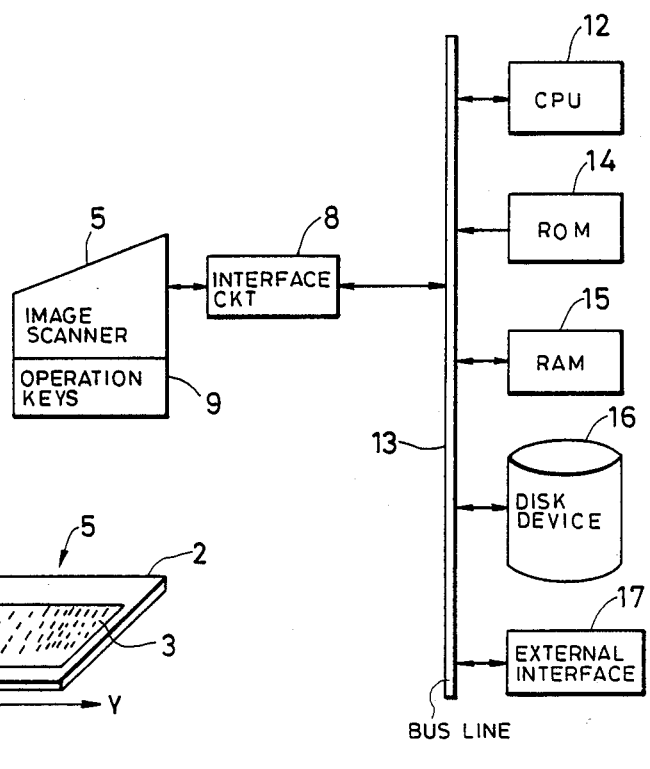
FIG. 1A is a block diagram of an apparatus for automatically reading a band arrayal pattern according to the present invention.
Figure 1B:
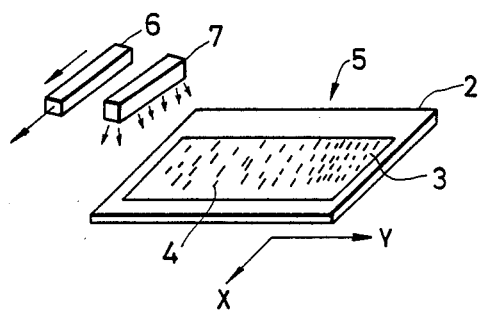
FIG. 1B is a view showing the essential portions of an image scanner 5 employed in the apparatus of FIG. 1A.
Figure 1C:
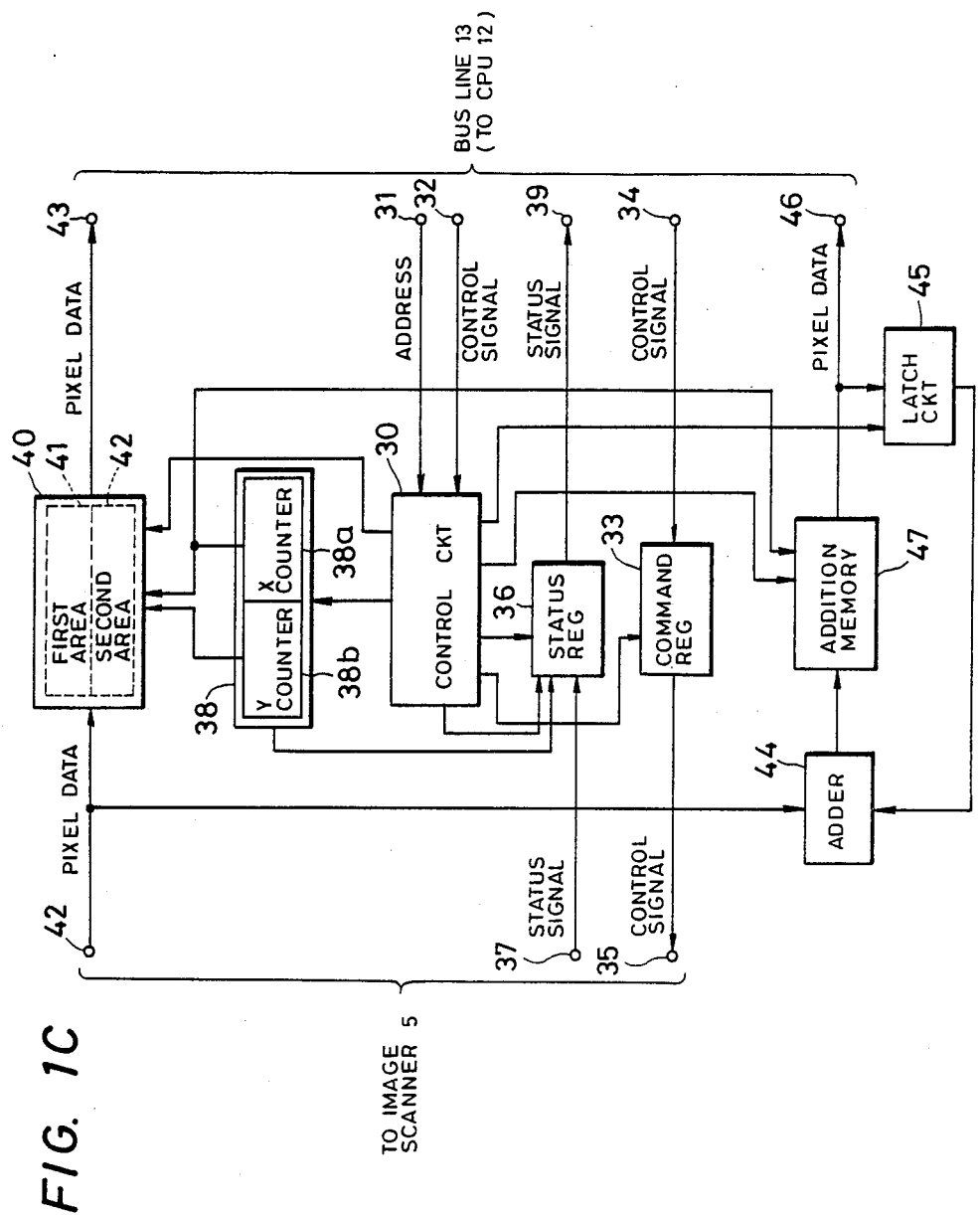
FIG. 1C is a block diagram of an interface circuit 8 in the apparatus of FIG. 1A.

FIG. 1A is a block system diagram of an embodiment of a band arrayal pattern-reading apparatus according to the present invention, FIG. 1B is a view showing the schematic arrangement of an image scanner 5, and FIG. 1C is a diagram showing the internal arrangement of an interface circuit 8.

Numeral 3 designates an X-ray film, on which bands 4 in solid lines corresponding to the four kinds of base codes A, C, G and T with their arrayal determined by the shotgun method, are arrayed and imaged.

This X-ray film 3 is positioned so that the lengthwise direction of lanes, being the valid ranges of the respective bases A, C, G and T, may come into substantial agreement with the direction of the Y-axis of the image scanner 5.

Numeral 2 designates a plate of transparent glass, which is set in the image scanner 5 and on which the X-ray film 3 is placed. The size of the transparent glass 2 is, for example, A3-size or so.

A unidimensional image sensor 6 is disposed in correspondence with the position of the transparent glass 2.

A unidimensional light emitting device 7 projects light on the X-ray film 3. Then, reflected light corresponding to one line in the direction of the X-axis of the X-ray film 3 enters the image sensor 6.

The image sensor 6 photoelectrically converts the reflected light for one line into pixel units, and thereafter derives electric signals serially by the use of a charge coupled device (CCD) or the like (not shown) built therein. It A/D-converts the derived electric signals into digital signals of, for example, 8 bits and delivers these signals. The image sensor 6 and the light emitting device 7 are moved at equal speeds in the Y-axial direction by a driving mechanism (not shown) so as to read the X-ray film 3 and detect the bands.

The image scanner 5 is constructed as shown in FIG. 1B. It reads the X-ray film 3, and delivers pixel data, being the read result.

Shown at numeral 9 are operation keys, which include a start key etc. The depression of this start key starts the reading processing of the X-ray film 3.

The interface circuit 8 has an image memory, an addition memory etc. built therein. It is connected to the image scanner 5 as well as to the operation keys 9, and it forms the interface between the image scanner 5 and a CPU 12 through a bus line 13.

The CPU 12 serves to execute the reading of the band arrayal and the corrections of the positions of the read bands.

Numeral 14 indicates a ROM in which a program for load is stored.

Numeral 16 indicates a disk device, in which a band arrayal reading program is stored and also base code data having been read is stored. When the power source of the reading apparatus is closed, the loading program stored in the ROM 14 is run, and the band arrayal reading program stored in the disk device 16 is loaded in a RAM 15.

The RAM 15 has an area SD for storing base data, an area for a band interval function, etc.

Numeral 17 denotes an external interface, which serves to transmit the read base code data to an external computer (not shown).

The interface circuit 8, CPU 12, ROM 14, RAM 15, disk device 16 and interface portion 17 are interconnected through the bus line 13.

Owing to the arrangement as thus far described, the image scanner 5 supplies the interface circuit 8 with the pixel data after it has photoelectrically converted the image of the X-ray film 3 on the transparent glass 2 into pixel units.

In addition, the loading program stored in the ROM 14 is run, and the band arrayal reading program stored in the disk device 16 is loaded in the RAM 15.

Subsequently, the CPU 12 executes the band arrayal reading program loaded in the RAM 15 and delivers various control signals to the interface circuit 8 through the bus line 13. The pixel data applied to the interface circuit 8 is processed on the basis of the control signals.

Thereafter, the base data being the processed result, is output to, for example, an external computer (not shown) through the external interface 17.

Now, the internal arrangement of the interface circuit 8 will be described with reference to FIG. 1C.

Numeral 30 designates a control circuit, which supplies operation control signals to an address counter 38, a status register 36, a command register 33, an addition memory 47 and a latch circuit 45 in accordance with an address signal and a control signal respectively applied from the CPU 12 to terminals 31 and 32 through the bus line 13.

The command register 33 is connected to the control circuit 30. It stores control signals for the image scanner 5 and the driving mechanism (not shown) thereof applied to a terminal 34, and supplies the control signals to the image scanner 5 and the driving mechanism through a terminal 35 in accordance with the operation signals received from the control circuit 30.

The status register 36 is connected to the address counter 38 and the control circuit 30. It stores the status signals of the image scanner 5 and the driving mechanism thereof applied to a terminal 37 and the status signals of the control circuit 30 and the address counter 38 inside the interface circuit 8, and supplies the status signals via a terminal 39 to the CPU 12 through the bus line 13 under the control of the control circuit 30.

The address counter 38 is connected to an image memory 40, the control circuit 30, the status register 36 and the addition memory 47. It is constructed of an X-counter 38a, which counts clock pulses supplied from the control circuit 30 and generates an address corresponding to a pixel position on one line in the X-axial direction, and a Y-counter 38b, which counts the carry pulses of the X-counter and generates an address corresponding to a pixel position in the Y-axial direction. The output addresses of the X-counter 38a and Y-counter 38b are supplied to the image memory 40, and the output address of the X-counter 38a is further supplied to the addition memory 47.

The image memory 40 consists of a first area 41 and a second area 42, and is connected to the address counter 38 and the control circuit 30. It stores pixel data applied from a terminal 42, in accordance with the X and Y addresses set by the address counter 38, and it reads out the stored pixel data and supplies the read data to the CPU 12 through a terminal 43 in accordance with the operation control signal received from the control circuit 30.

Shown at numeral 44 is an adder, which is connected to the terminal 42, the addition memory 47 and the latch circuit 45. It adds the pixel data received from the terminal 42 and addition pixel data latched in the latch circuit 45, and delivers the result to the addition memory 47.

The addition memory 47 is connected to the adder 44, the address counter 38, the control circuit 30 and the latch circuit 45. The addition pixel data delivered from the adder 44 is stored in the addition memory 47 in correspondence with the X address supplied from the address counter 38, and it is read out to be delivered to the latch circuit 45 and also supplied to the CPU 12 through a terminal 46 in accordance with the operation control signal received from the control circuit 30.

The latch circuit 45 is connected to the control circuit 30, the adder 44 and the addition memory 47. It latches the addition pixel data read out from the addition memory 47, and delivers the latched addition pixel data to the adder 44 in accordance with the latch pulse received from the control circuit 30.

Next, an embodiment of the band arrayal reading program which is run by the CPU 12 will be described with reference to FIG. 3A.

Figure 3A:
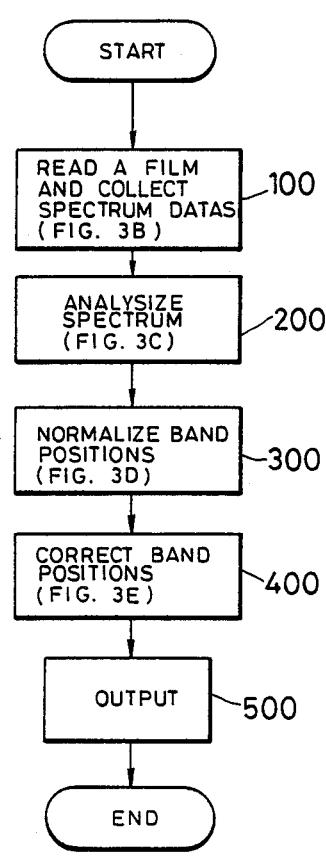
FIG. 3A is a flow chart of a band arrayal reading program which is run by a CPU 12 in FIG. 1A.

When an operation signal generated by depressing the start key among the operation keys 9 is supplied to the CPU 12 through the interface circuit 8, the CPU 12 starts processing shown in FIG. 3A. At a step 100, the reading of the X-ray film 3 and the collection of spectral data are executed by the image sensor 6.

At a step 200, a spectrum obtained at the step 100 is analyzed to detect band positions.

At a step 300, the band positions detected at the step 200 are normalized.

At a step 400, base code data is corrected. That is, base data is checked, base data detected erroneously is erased, and base data having failed to be detected is compensated for.

At a step 500, the base data items are read out in the order of addresses corresponding to the Y-axial direction, to be stored in the disk device 16 and to be transmitted from the external interface 17 to the external computer (not shown).

Figure 2A:
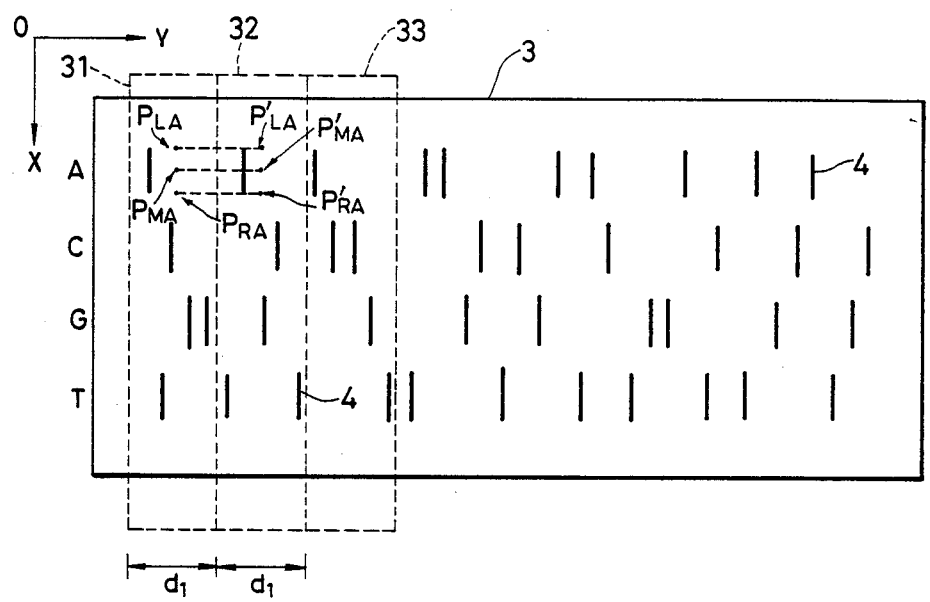
FIG. 2A is a diagram showing an example of a band arrayal pattern which is read by the apparatus of FIG. 1A.

FIG. 2A shows the X-ray film 3, on which the plurality of bands 4 are arrayed in correspondence with each of the bases A, C, G and T.

Figure 2B:
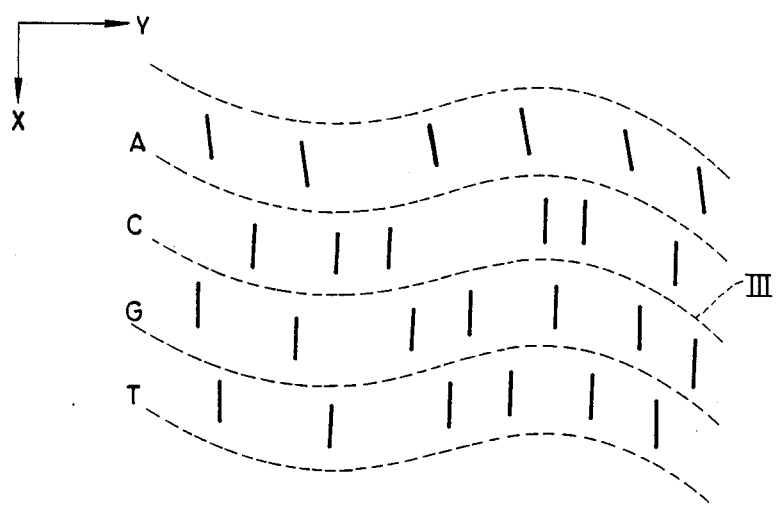
FIG. 2B is a diagram showing another example of a band arrayal pattern.

FIG. 2B similarly shows the X-ray film 3. In this case, however, the respective lanes are not rectilinear but are meandering. With the X-ray film 3 having the meandering lanes in this manner, when the spectral data items are collected assuming the lanes in the whole X-ray film to be rectilinear, it becomes impossible to discriminate the lane of the base to which the spectrum collected near the boundary of the adjacent lanes indicated by a broken line in FIG. 2B belongs.

Therefore, the X-ray film 3 is divided every fixed section $d_1$ in the Y-axial direction as indicated by dotted lines in FIG. 2A, a histogram is prepared for each divided section $d_1$, the histogram is analyzed to detect the X-axial positions of the respective lanes of the base codes A, C, G and T, and the lanes are thereafter sampled.

Thus, even when the lanes of the bases A, C, G and T shift and meander in the X-axial direction as illustrated in FIG. 2B, the spectra of the respective lanes can be accurately collected.

Figure 3B:
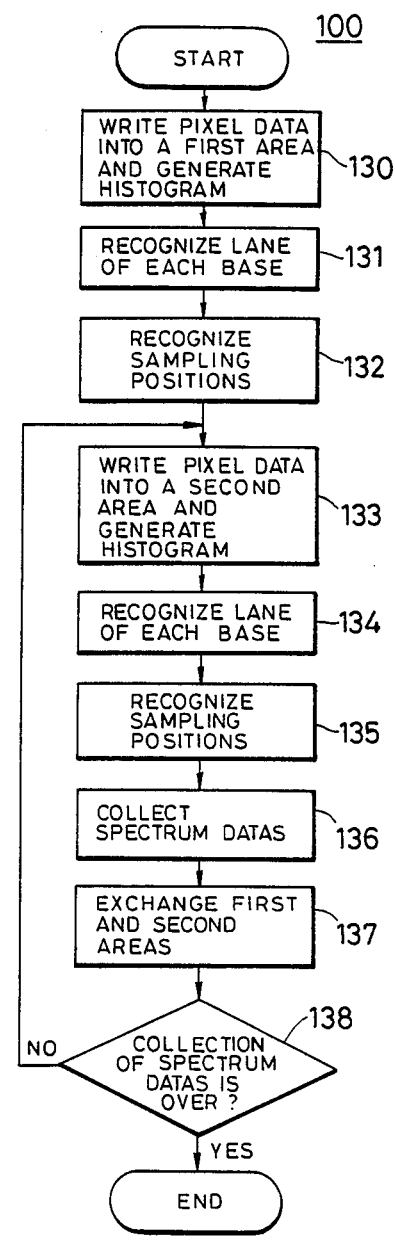
FIG. 3B is a flow chart of processing which is executed by step 100 in FIG. 3A.

FIG. 3B is a flow chart of the processing which is executed at the step 100. The processing of the film reading and the spectrum collection to be executed by this flow chart will be described with reference to FIG. 1C.

At a step 130, the CPU 12 supplies a control signal to the image sensor 6 through the interface circuit 8, whereby the image sensor 6 is moved at a fixed speed by the distance $d_1$ (for example, several tens mm) in the Y-axial direction by means of the driving mechanism (not shown). Each time the image sensor 6 is moved by a minute distance $d_2$ (for example, $d_2 = 1/16$ mm), it serially delivers pixel data (detection data) corresponding to one line in the X-axial direction. The pixel data items are supplied to the interface circuit 8, and are successively written into the image memory 40 built in the interface circuit 8. Besides, the pixel data is added by the adder 44 in the interface circuit 8 with addition pixel data read out from the address of the addition memory 47 corresponding to each detection position of one line in the X-axial direction, and the result is stored in the same read-out address of the addition memory 47.

That is, at the same time that the image sensor 6 reads the pixel data for the distance $d_1$, the addition data items, each being the sum of the pixel data for the minute distance $d_2$ in the Y-axial direction, are stored in parallel into the addresses of the addition memory 47 corresponding to the respective detection positions of one line in the X-axial direction, and a histogram is obtained.

Here, the processing of the step 130 will be described in detail with reference to time charts in FIGS. 4A–4F.

Figure 4A:
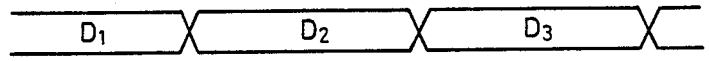
Figure 4B:
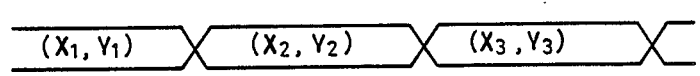
Figure 4C:
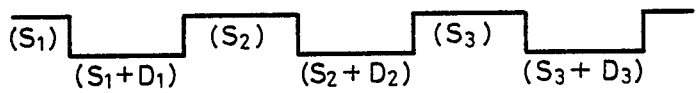

Pixel data items $D_1$, $D_2$ and $D_3$, serially transmitted as shown in FIG. 4A, are input to the terminal 42 shown in FIG. 1C, and are supplied to the image memory 40 and the adder 44. In synchronism with the pixel data items, the X counter 38a of the address counter 38 changes its output address value as shown in FIG. 4B. Besides, the control circuit 30 supplies the addition memory 47 with an operation control signal (write strobe) as shown in FIG. 4C, and the addition memory 47 writes data in the low level interval of the write strobe and reads data in the high level interval thereof. The image memory 40 is also supplied with the same write strobe as shown in FIG. 4C, and data is written into the image memory 40 in the low level interval of the write strobe.

Figure 4D:
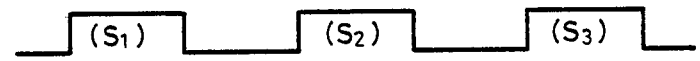
Figure 4E:
Figure 4F:
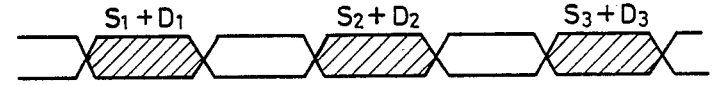

The addition memory 47 has addresses corresponding to the respective detection positions of one line in the X-axial direction, and the contents of all the addresses are cleared to zero when the CPU 12 commands the image sensor 6 to start reading. Thereafter, the addition memory 47 reads out addition pixel data stored in the address designated by the X counter 38a, in the high level interval of the write strobe shown in FIG. 4C. The latch circuit 45 is supplied from the control circuit 30 with latch pulses which are obtained by inverting the write strobe as shown in FIG. 4D. It latches the addition pixel data at the point of time of the rise of the latch pulse, namely, at the point of time of the end of the reading of the addition memory 47. Thus, the addition pixel data is supplied from the latch circuit 45 to the adder 44. The addition pixel data changes as shown in FIG. 4E. Accordingly, the addition pixel data which is the addition value between the pixel data applied from the terminal 42 to the adder 44 and the addition pixel data from the latch circuit 45 changes as shown in FIG. 4F. In the addition pixel data, addition pixel data items hatched are written into the addition memory 47 in the low level intervals of the strobe shown in FIG. 4C.

In this manner, the read pixel data $D_1$ and the output $S_1$ of the latch circuit 45 are added by the adder 44, and the resulting addition pixel data ($S_1 + D_1$) is written into the image memory 47 in the low level interval of the write strobe in FIG. 4C.

Letting $S_2$ denote the addition pixel data ($S_1 + D_1$), this addition pixel data $S_2$ is latched in the latch circuit 45 at the point of time of the end of the high level interval of the write strobe in FIG. 4C, whereupon the read pixel data $D_2$ and the output $S_2$ of the latch circuit are added and are written into the image memory 47 as addition pixel data ($S_2 + D_2$).

Next, letting $S_3$ denote the addition pixel data ($S_2 + D_2$), the read pixel data $D_3$ and the output $S_3$ of the latch circuit are similarly added and written into the image memory 47 as addition pixel data ($S_3 + D_3$).

By repeating such processing steps, the pixel data items are added.

When the image sensor 6 has moved by the distance $d_1$ in this way, the addition pixel data or the histograms which are the summations of the pixel data provided every minute distance $d_1$ in the Y-axial direction are stored in the addresses of the addition memory 47 corresponding to the respective pixel positions (detection positions) in the X-axial direction.

Meanwhile, the image memory 40 is divided into the first area 41 and the second area 42 in accordance with the most significant bit of the output address of the Y counter 38b. When the CPU 12 first commands the image sensor 6 to read the data, the value of the most significant bit is "0" and the first area 41 is selected. Thereafter, each time the reading is commanded, the value of the most significant bit changes. That is, the area 41 is selected for the most significant bit of "0," and the area 42 for the most significant bit of "1." The address of the address counter 38 to be supplied to the image memory 40 is incremented each time the pixel data is input from the terminal 42. The pixel data items obtained while the image sensor 6 is first moved by the distance $d_1$ as described above (for example, data items within a partial area 31 in FIG. 2A) are all stored in the first area 41. The pixel data items obtained while the image sensor 6 is subsequently moved by the distance $d_1$ (for example, data items within a partial area 32 in FIG. 2A) are all stored in the second area 42

In this manner, at the same time that the pixel data items from the X-ray film 3 are read and written into the image memory 40, the pixel data items of the predetermined section (of the distance $d_1$) in the Y-axial direction are added for the respective pixel positions in the X-axial direction, and the results are written into the addition memory 47 to generate the histograms. The above is the contents of the step 130.

In order to recognize the lanes, histograms need to be obtained in such a way that the values of pixel data in the predetermined section $d_1$ in the Y-axial direction of the lanes are added for pixel positions in the X-axial direction of the lanes of the respective bases A, C, G and T. In this case, the read pixel data items are added for the respective pixel positions in the X-axial direction by means of the adder 44, whereby addition pixel data or the histograms for the respective pixel positions in the X-axial direction are obtained simultaneously and in parallel with the reading of the pixel data.

The generation of the histograms is performed fast by the hardware of the adder 44 etc., and can therefore be processed simultaneously and in parallel with the writing of the pixel data into the image memory 40.

Besides, the generation of the histograms is performed by the addition memory 47 as well as the single adder 44 and the latch circuit 45 attendant thereon, so that the number of components is small and the circuit arrangement is simple.

In this manner, simultaneously and in parallel with the reading of the pixel data for the distance $d_1$ by the image sensor 6, the addition data items, which are the sums of the pixel data obtained every minute distance $d_2$ in the Y-axial direction, are stored in the addresses of the addition memory 47 corresponding to the respective detection positions of one line in the X-axial direction, and the histograms are generated.

When the histograms stored in the addition memory 47 are converted into an analog quantity, a waveform as shown in FIG. 5A is obtained. At a step 131, the CPU 12 differentiates the histograms of the addition memory 47 with respect to the X direction, to obtain differential values of which become a waveform as shown in FIG. 5B, and it stores the differential values in a working area (not shown) within the RAM 15. Further, with reference to the plus maximum value and minus maximum value of the differential values, a plus threshold value THH and a minus threshold value THL, which are respectively equal to $\frac{1}{2}$ of the plus and minus maximum values by way of example, are set. Thereafter, the values of points at which the differential values exceed the plus threshold value THH and points at which they become less than the minus threshold value THL, $x_{LA}$, $x_{RA}$, $x_{LC}$, $x_{RC}$, $x_{LG}$, $x_{RG}$, $x_{LT}$ and $x_{RT}$ are found and are recognized as the positions of the X-axial left and right ends of the lanes of the respective base codes A, C, G and T in the partial region 31 (FIG. 2A) (step 131). Subsequently, the values of the middle points $x_{MA}$, $x_{MC}$, $x_{MG}$, and $x_{MT}$ of the respective points $x_{LA}$ and $x_{RA}$, $x_{LC}$ and $x_{RC}$, $x_{LG}$ and $x_{RG}$, and $x_{LT}$ and $x_{RT}$ are calculated. The points $x_{Li} - x_{Ri}$ (i=A, C, G, T) are recognized as sampling positions (step 132).

Thereafter, the CPU 12 further moves the image sensor 6 by the distance $d_1$ in the Y-axial direction. It stores pixel data delivered from the image sensor 6, in the second area 42 of the image memory 40 in succession and also stores addition pixel data as histograms in the addition memory 47 (step 133). Thereafter, in the same way as at the 30 step 131, the values of the left ends and right ends $x'_{Li} - x'_{Ri}$ (i=A, C, G, T) of the respective lanes are found and are recognized as the positions of the lanes of the respective bases (step 134). Further, the middle points $x'_{Mi}$ (i=A, C, G, T) of the respective lanes in the second partial region 32 (FIG. 2A) are found on the basis of the values of the above points, whereby the values of all sampling positions $x'_{Li, Mi, Ri}$ (i=A, G, C, T) are found.

Here, even when a specified lane has no band to-be-extracted in the region subjected to the addition, a significant difference between a density value in the lane and a density value in the background outside the lane is obtained in the addition histogram because the density value in the lane is greater than the density value in the background, so that the lane can be usually found. However, in a case where the difference is not obtained in the addition histogram for such a reason that the difference of the density values in the lane and in the background is less than the sensitivity of a detector, the boundary values of the lane found in the preceding predetermined section may be utilized. Besides, when a small section where the lane is not found is the first small section, the boundary values of the lane may be set by proportionally assigning the interspace between found lanes corresponding to other bases. By way of example, when two lanes are not found, a section where they are not found may be divided in two, the middles of the divided parts being set as the centers of the lanes.

Since the sampling positions $x_{Li}$, $x_{Mi}$, $x_{Ri}$ and $x'_{Li}$, $x'_{Mi}$, $x'_{Ri}$ (i=A, C, G, T) mentioned above have been obtained on the basis of the addition values for the Y-axial distance $d_1$, they can be regarded as the positions $p_{Li}$, $p_{Mi}$, $p_{Ri}$, $p'_{Li}$, $p'_{Mi}$ and $p'_{Ri}$ (i=A, C, G, T) of the left ends, centers and right ends of the respective lanes at the middle positions of the first and second partial regions 31 and 32 in the Y-axial direction. Accordingly, when the pixel data items on lines connecting the points $p_{Li}$ and $p'_{Li}$, $p_{Mi}$ and $p'_{Mi}$, and $p_{Ri}$ and $p'_{Ri}$ are read out from the image memory 40, pixel data trains (spectra) at the left end, center and right end of each lane are obtained.

Meanwhile, at this time, the pixel data items of the first and second partial regions 31 and 32 (FIG. 2A) of the film 3 are respectively being stored in the first and second areas 41 and 42 of the image memory 40. For this reason, the CPU 12 collects the spectral data between the points $p_{LA}$ and $p'_{LA}$ in such a way that the pixel data items of positions (addresses) corresponding to the line connecting the points $p_{Li}$ and $p'_{Li}$ are read out successively in a direction from the point $p_{Li}$ to the point $p'_{Li}$ and are successively written into predetermined addresses within the RAM 15. Likewise, the spectral data items between the points $p_{MA}$ and $p'_{MA}$ and between the points $p_{RA}$ and $p'_{RA}$ are collected. The same is performed for the other lanes (step 136). Thus, each of the base codes A, C, G and T has the spectral data collected at the three points of both the ends and the middle of the band. Thereafter, the first area 41 and second area 42 of the image memory 40 are exchanged and used (step 137). Next, it is decided whether or not the image sensor 6 has scanned to the right end of the transparent glass 2 shown in FIG. 1B, so the collection of the spectral data of the whole area of the X-ray film 3 is over (step 138). When the collection is not over, the processing control proceeds to the step 133. Here, the first area 41 and second area 42 of the image memory 40 have been exchanged at the step 137. At the step 133, therefore, the pixel data items of the region 33 (FIG. 2A) of the next distance $d_1$ are successively written into the area (for example, the first area 41) opposite to the area (for example, the second area 42) within the image memory 40 in which the pixel data items were written at the preceding time. In this way, the steps 133–137 are repeatedly executed thereby to collect the spectral data of the whole area of the X-ray film 3. Then, the step 100 ends.

At the step 100, spectral data items $S_{Li}$, $S_{Mi}$ and $S_{Ri}$ (i=A, C, G and T) of the three sorts; the left end, center and right end for each of the bases A, C, G and T, totaling twelve sorts are collected and are stored in the RAM 15 in the order of the Y-axial positions of the respective pixels.

Figure 3C:
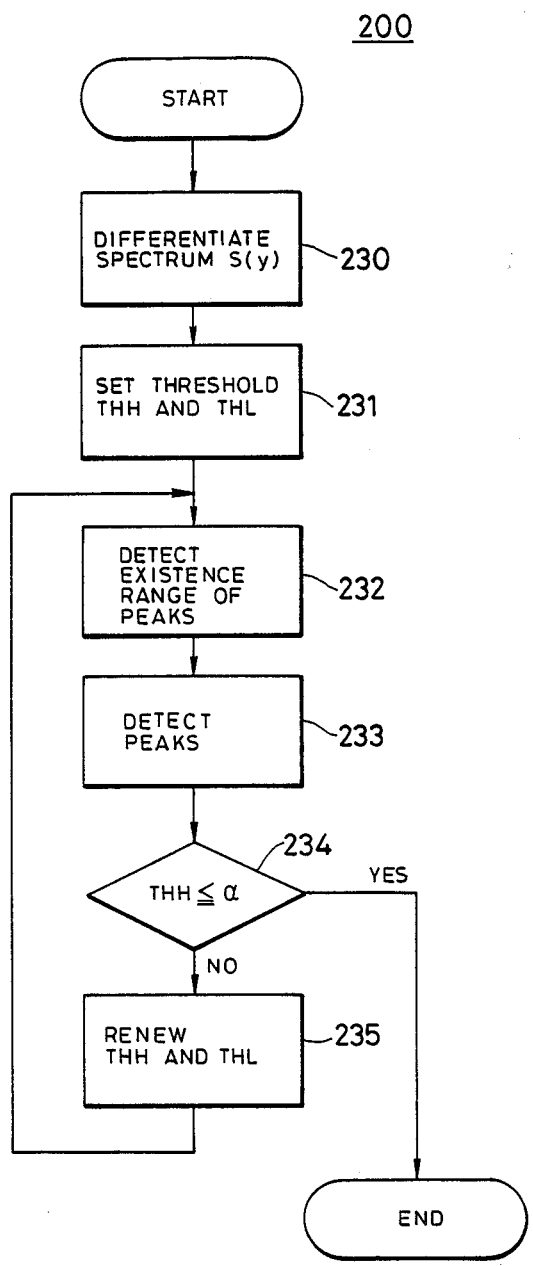
FIG. 3C is a flow chart of processing which is executed by step 200 in FIG. 3A.

At the next step 200, the spectra $S_{Li}$, $S_{Mi}$ and $S_{Ri}$ (i=A, C, G, T) are respectively analyzed to detect band positions. FIG. 3C shows the detailed flow chart of the processing 200. When the spectra $S_{Li}$, $S_{Mi}$ and $S_{Ri}$ (i=A, C, G, T) are respectively converted into analog quantities S(y), they become a waveform as shown in FIG. 6A. At a step 230 in FIG. 3C, the CPU 12 reads out the respective spectra S(y) from the RAM 15 and differentiates them to obtain differential spectra S'(y) the analog conversion values of which become a waveform shown in FIG. 6B. Thereafter, with reference to the plus maximum value and minus maximum value of the differential spectra S'(y), a plus threshold value THH and a minus threshold value THL, which are respectively equal to ½ of the plus maximum value and minus maximum value by way of example, are set (step 231).

Subsequently, Y-axial values $y_1$, $y_4$, $y_7$ . . . , at which the differential spectra S'(y) change from a value not less than the plus threshold value THH to a value less than the same and Y-axial values $y_3$, $y_6$, $y_9$ . . . , at which the differential spectra S'(y) change from a value not less than the minus threshold value THL to a value less than the same, are found to detect the existence ranges of peaks $y_1$–$y_3$, $y_4$–$y_6$, $y_7$–$y_9$, . . . (step 232). Parts indicated by dotted lines in FIGS. 6A and 6B are the existence ranges of peaks. Thereafter, as to the existence range of a peak $y_1$–$y_3$, a Y-axial value $y_2$, at which the differential spectrum S'(y) is zero and accordingly the spectrum S(y) become, the a maximum, is found. Likewise, Y-axial values $y_5$, $y_8$, . . . , at which the differential spectrum S'(y) is zero and accordingly the spectrum S(y) becomes a maximum found in the respective existence ranges of peaks $y_4$–$y_6$, $y_7$–$y_9$, . . . (step 233). The values $y_3$, $y_5$, $y_8$, . . . obtained here are the positions of the peak points.

The reason why the peak existence range is first detected in this manner is as follows: The spectrum S(y) might contain noise N attributed to dust etc. Therefore, an erroneous band position will be detected merely by finding only the value at which the differential spectrum S'(y) is zero.

In order to prevent such detection of the erroneous band position, accordingly, the plus threshold value THH and minus threshold value THL are set, and the peak existence range is obtained, whereupon the value at which the differential spectrum S'(y) is zero is found within the peak existence range. Therefore, the noise N is not detected as a band position.

In this way, an analytical spectrum SS(y), expressive of the band positions as shown in FIG. 6(C), is obtained. For instance, FIG. 6D shows the analytical spectra SS(y) expressive of the band positions as obtained for the respective bases A, G, T and C. The analytical spectra SS(y) are stored in the RAM 15 as a table wherein addresses are assigned to the respective pixels in the Y-axial direction and wherein the value of the existence position of the band is "1" and that of the non-existence position thereof is "0", by way of example.

Further, the position of the spectrum corresponding to the band has a certain width in the Y-axial direction as shown by S(y) in FIG. 6A. The width differs for the individual bands, and also the density values of the individual bands differ. Therefore, the band existence range is detected using the differential spectrum S'(y), and the point at which the differential spectrum S'(y) is zero and accordingly the spectrum S(y) becomes the maximum is detected as the band position from within the band existence range, whereby the existence position of the band can be accurately specified irrespective of the density of the band and the magnitude of the band width.

After the peak detection, the plus threshold value THH is compared with a predetermined value α (step 234). When the plus threshold value THH is greater, the processing flow shifts to a step 235. At the step 235, the plus threshold value THH and minus threshold value THL are updated to, for example, ½ of the respective values used till then, whereupon the processing flow shifts to the step 232. Thus, the peak detection is repeated using the new plus threshold value THH and minus threshold value THL (step 233). Herein, the processing of detecting peaks is not performed in the existence ranges $y_1$–$y_3$, $y_4$–$y_6$ and $y_7$–$y_9$ found at the step 232 in the last analyzing process. When it is decided at the step 234 that the plus threshold value THH is not greater than the predetermined value α, the processing of FIG. 3C for one spectrum ends. Here, the predetermined value α has its lower limit set at a value with which the noise N is not detected as a band position, and while the value is being updated, probable band positions are found in succession. The processing of FIG. 3C is performed for all the spectra $S_{Li}$, $S_{Mi}$ and $S_{Ri}$ (i=A, C, G, T), and the analytical spectra $SS_{Li}$, $SS_{Mi}$ and $SS_{Ri}$ (i=A, C, G, T) which are band detection information are obtained.

Figure 3D:
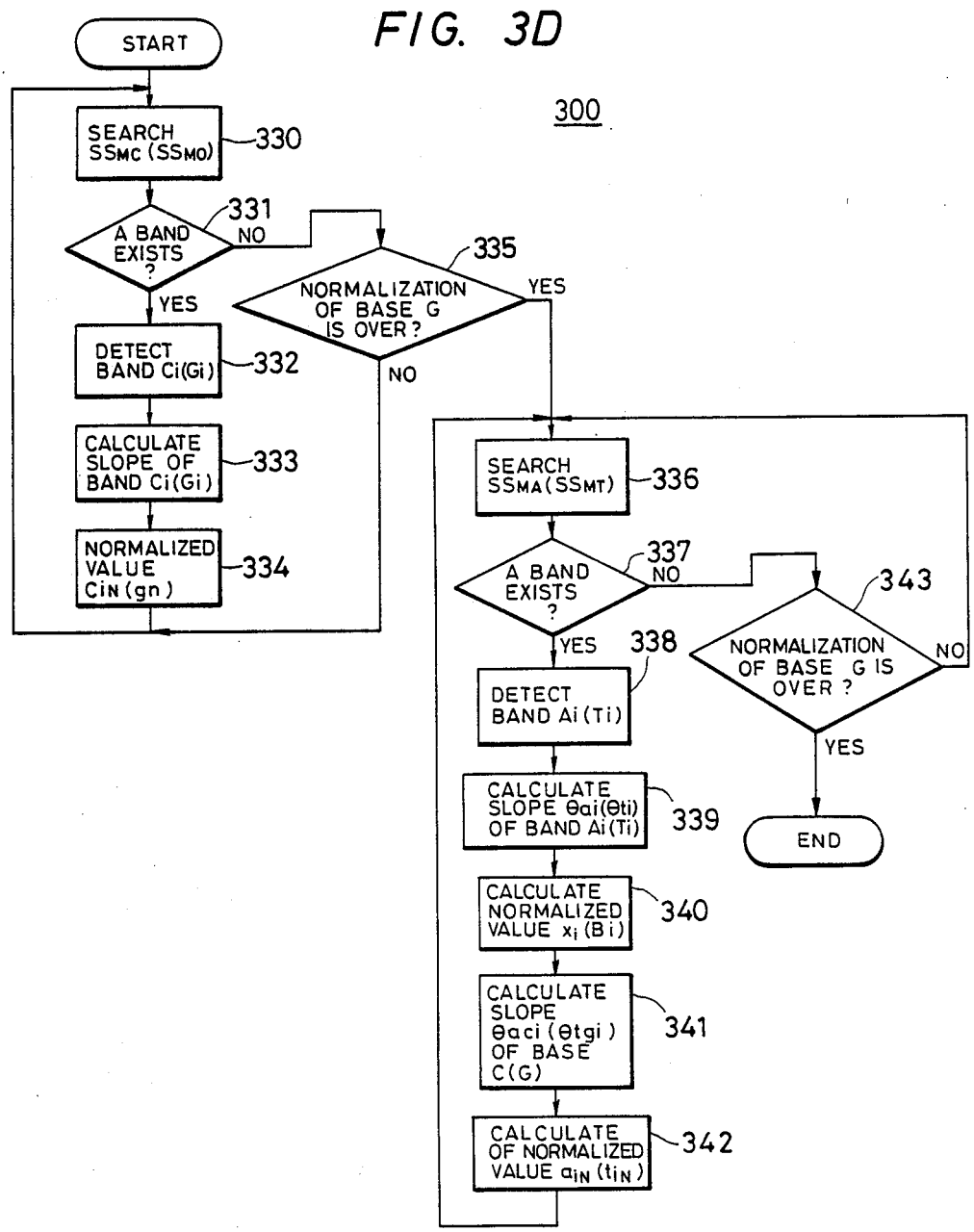
FIG. 3D is a flow chart of processing which is executed by step 300 in FIG. 3A.

At the next step 300, the band positions are normalized by a routine shown in FIG. 3D.

Figure 7:
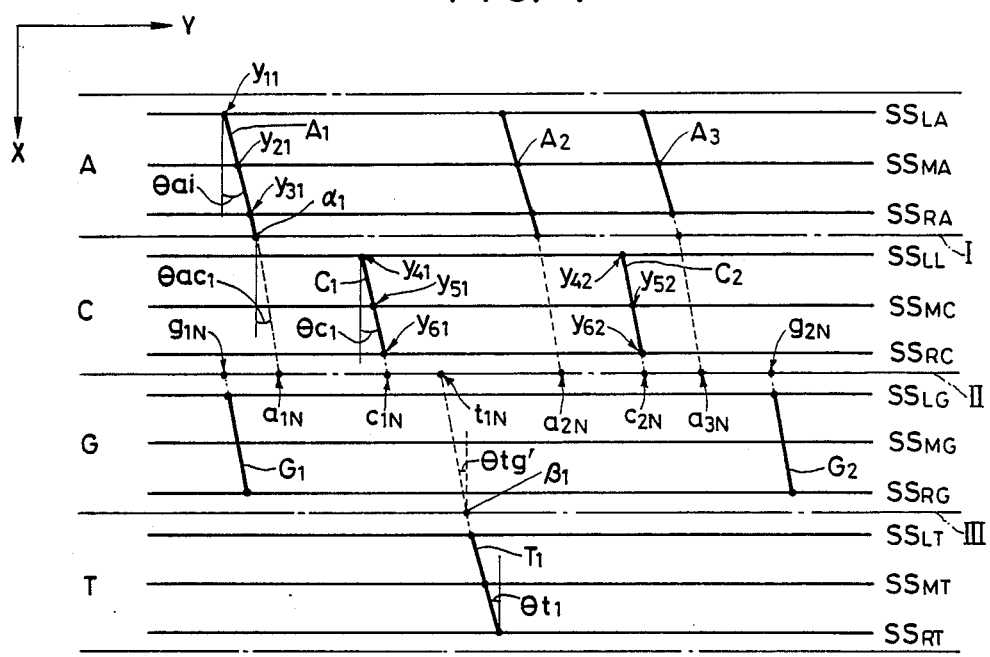
FIG. 7 is a diagram for explaining the normalization of band positions according to the apparatus of FIG. 1A.

The normalization of the band positions is carried out for the purpose of accurately reading the band arrayal order of the base codes even in a case where the respective bands 4 of the bases A, C, G and T incline as shown in FIG. 7.

Referring to FIG. 3D, as regards the base C, the analytical spectrum $SS_{MC}$ within the RAM 15 is searched in the Y-axial direction, and the address of the analytical spectrum $SS_{MC}$ having the value "1," namely the value $y_{51}$ of a Y-axial position shown in FIG. 7, is found (step 330). At a step 331, whether the analytical spectrum $SS_{MC}$ of the value "1" has been searched is decided. When it has been searched, the processing flow shifts to a step 332. At the step 332, the Y-coordinate values $y_{41}$ and $y_{61}$ points at which the values of the analytical spectra $SS_{LC}$ and $SS_{RC}$ become "1" are respectively found near (in the Y-axial direction) the value $y_{51}$ found by the search. Then, the positions of the left end, center and right end ($y_{41}$, $y_{51}$, $y_{61}$) of the band C are detected. Of course, in a case where the values $y_{41}$ and $y_{61}$ cannot be obtained, the value $y_{51}$ is recognized as an error, and the existence of the band C is not detected. Thereafter, the slope $\theta_{C1}$ of a straight line passing the three points $y_{41}$, $y_{51}$ and $y_{61}$ on the detected band $C_1$ is calculated (step 333).

Next, using the value $y_{51}$ and the slope $\theta_{C1}$, the value (normalized value) of the Y-axial position $C_{1N}$ of the band $C_1$ at the boundary II (FIG. 7) of the base codes C and G is calculated (step 334). Thereafter, the processing flow shifts to the step 330, and the steps 330–334 are repeatedly executed, whereby normalized values $C_{2N}$, ... are found. When the search of the spectrum $SS_{MC}$ is over, the processing of FIG. 3D for the base C is over. Thereafter, whether the processing of FIG. 3D has been executed for the base G or not is decided (step 335). When it has not been executed, normalized positions $g_{1N}$, $g_{2N}$, ... are similarly found. Thereafter, as regards the base A, the analytical spectrum $SS_{MA}$ is searched in the RAM 15 (step 336). When the value, e.g., $y_{21}$ of the Y-axial position of the analytical spectrum $SS_{MA}$ has been found (step 337), values $y_{11}$ and $y_{31}$ at which the values of the analytical spectra $SS_{LA}$ and $SS_{RA}$ become "1" are respectively found near (in the Y-axial direction) the above value $y_{21}$, to detect the positions ($y_{11}$, $y_{21}$, $y_{31}$) of the band $A_1$ (step 338). Further, the slope $\theta_{a1}$ of a straight line passing the values $y_{11}$, $y_{21}$ and $y_{31}$ of the three points of the band $A_1$ is calculated (step 339). Besides, using the value $y_{31}$ and the slope $\theta_{a1}$, a quasi-normalized value $\alpha_1$ at the boundary I of the base codes A and C is calculated (step 340).

Here, the lanes sometimes meander as shown in FIG. 2B, and the boundary of the detected lanes inclines on this occasion. Even in that case, the band detected at the step 338 can be regarded as the straight line with a slope $\theta_{a1}$ calculated at the step 339, so that the quasi-normalized value $\alpha_1$ can be readily found by obtaining the intersection point between this band and the boundary. Subsequently, the slope $\theta_{Ci}$ ($\theta_{C1}$ in this example) of the band $C_i$ ($C_1$ in this example) of the base code C at a position nearest to the quasi-normalized value $\alpha_1$ is found in each of X-axial parts greater and smaller than the quasi-normalized value $\alpha_1$ which is the value of the Y-axial position. Using the quasi-normalized value $\alpha_1$ the slope $\theta_{Ci}$, the slope $\theta_{ac1}$ of the position corresponding to the quasi-normalized value $\alpha_1$ of (the lane of) the base code C is found (step 341). Further, the quasi-normalized value $\alpha_1$ and the slope $\theta_{ac1}$ are used to find the Y-coordinate value of the normalized position $a_{1N}$ of the band $A_1$ at the boundary II (step 342). Thereafter, the processing flow shifts to the step 336, and the steps 336–342 are repeatedly executed, whereby the Y-coordinate values of the normalized positions $a_{2N}$ and $a_{3N}$ of the respective bands $A_2$ and $A_3$ are obtained. After such normalization is over (step 343), the processing of FIG. 3D for the base code T is similarly performed to obtain normalized values $t_{1N}$, ...

The normalized values $a_{1N}$, $c_{1N}$, $g_{1N}$, $t_{1N}$ etc. obtained by the above processing of FIG. 3D are Y-axial values on the boundary II. An area SD within the RAM 15 is given addresses for the Y-axial direction on the boundary II. Base data items "A" are stored in the addresses of the area SD corresponding to the normalized positions $a_{1N}$, ... Likewise, base data items "C," "G" and "T" are respectively stored in the addresses for the normalized positions $c_{1N}$, ..., $g_{1N}$, ... and $t_{1N}$, ..

As described above, the bands 4 of the respective bases A, C, G and T are often slanted with respect to the boundaries of the lanes of the respective bases, and the slopes differ for the respective lanes. The bands are therefore normalized on the boundary II in accordance with the slopes thereof, whereby the band arrayal order of the bases can be correctly read even when the respective bands are slanted at individually differing angles.

Thus, the step 300 in FIG. 3A ends.

Thereafter, the base data items of the area SD within the RAM 15 are corrected at the step 400 in FIG. 3A.

More specifically, in a case where a band imaged on the X-ray film is thin, it is not detected. Besides, in a part of close band intervals, a plurality of bands are detected as a single band, and failure to detect one or more bands arises.

Further, a ghost band imaged on the X-ray film 3 and noise ascribable to dust etc. are detected as bands.

In the processing of the step 400, therefore, the interval of adjacent bands on a single line is compared with a minimum band interval and a reference band interval, and the band is erased or has its position corrected.

Figure 3E:
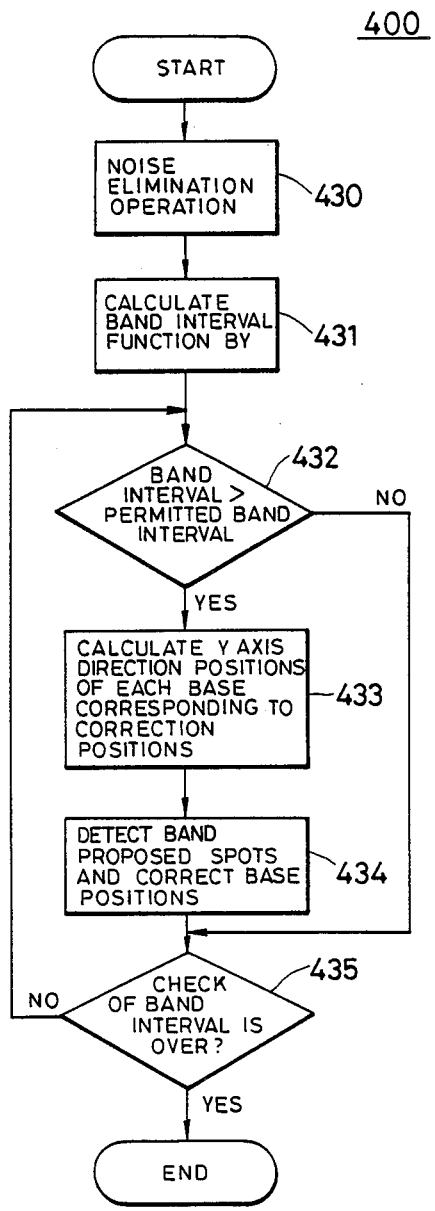
FIG. 3E is a flow chart of processing which is executed by step 400 in FIG. 3A.

Now, the processing of the step 400 will be described in detail with reference to FIG. 3E.

This figure shows a detailed flow chart of the processing of correcting the base data.

Figure 8:
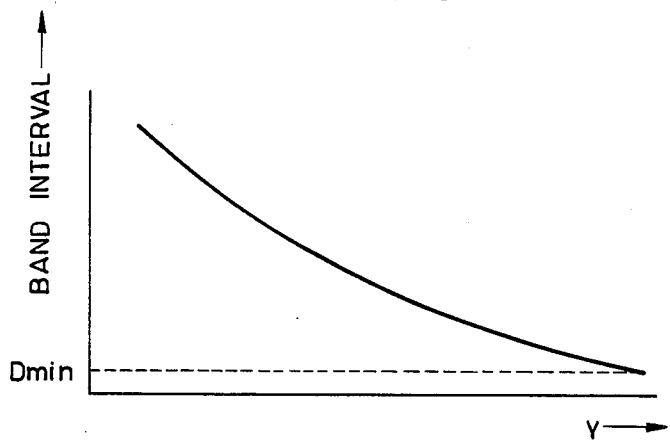
FIG. 8 is a diagram for explaining the correction of a band position detection error according to the apparatus of FIG. 1A.

The band intervals (in the Y-axial direction) of adjacent bands which have been read from the X-ray film 3 imaged by the shotgun method and which have been normalized on the boundary line indicated by the dot-and-dash line II in FIG. 7 have a relationship shown in FIG. 8 to the values of Y-axial positions. At a step 430 in FIG. 3E, the band intervals of the adjacent bands are successively found on the basis of the differences of the addresses of the area SD in which the base data items are stored, and they are compared with the minimum band interval $D_{min}$ in FIG. 8. In a case where the band interval found here is smaller than the minimum band interval $D_{min}$, the base data of that band of the adjacent bands used for finding the band interval as to which the value of the Y-axial position, namely the address value of the area SD is smaller, is regarded as noise and is erased from the area SD. The noise elimination processing stated above is performed for the whole area SD.

Subsequently, using the area SD subjected to the noise elimination processing, the band intervals of the adjacent bands are found by successively increasing the values of the Y-axial positions, namely, the addresses. A band interval function BY with the characteristic of FIG. 7 moved in parallel in the Y-axial direction (lateral direction in FIG. 7) is calculated according to the obtained band intervals of the bands, and it is stored in an area B for the band interval function within the RAM 15 having corresponding addresses in the Y-axial direction, as the reference band intervals in successive fashion (step 431).

The reason why the band interval function BY is found in this way is that the values in the Y-axial direction in FIG. 7 change depending upon the placed position of the X-ray film 3 on the transparent glass 2, and so on.

Subsequently, the band intervals of the adjacent bands are found by successively increasing the addresses of the area SD. The band interval is compared with a permissible band interval which is obtained in such a way that the reference band interval read out from the address of the area B corresponding to the value of the Y-axial position of the middle point of the adjacent bands is multiplied by a predetermined constant (step 432). When the band interval individually found on the basis of the address of the area SD is greater than the permissible band interval, failure to detect a band is decided, and the band is re-detected in the following way at steps 433 and 434. At the step 433, the slopes of the bands of the respective bases A, C, G and T corresponding to the Y-axial position of a correction point which is the middle point of the adjacent bands in the area SD are found by the same process for detecting the band positions as stated before, and the values (inverse normalized correction points) of the Y-axial position for the band centers ($x_{MA}$, $x_{MC}$, $x_{MG}$ and $x_{MT}$ in FIG. 5B) of the respective bases A, C, G and T corresponding to the first-mentioned correction point are found.

At the subsequent step 434, the value of the inverse normalized correction point of the spectrum $SS_{MA}$ is compared with a value equal to, e.g., ½ of the value of the spectrum $SS_{MA}$ recognized as a band near the inverse normalized correction point, and when the value of the spectrum at the inverse normalized correction point is greater, this inverse normalized correction point is deemed the band candidate point of the base A. Likewise, the band candidate points of the respective bases C, G and T are detected as to the spectra $SS_{MC}$, $SS_{MG}$ and $SS_{MT}$. In a case where the plurality of band candidate points have been obtained in this manner, the values of the spectra at the respective band candidate points are compared. Then, the base having the greatest spectral value is determined as a correction base, and correction base data is stored in the address of the area SD corresponding to the correction point. Here, in a case where it is previously known as to the property of the film that the spectral value increases or decreases depending upon the contents of the prior and posterior bands, a decision with the condition taken into consideration is effective. For example, under the known condition that, when the adjacent band is of the base A, the value of the adjacent base C becomes 30% smaller, or that a ghost appears (the value increases by 30%), the comparison is made after correcting the value of the base C. In a case where the step 432 has determined that the band interval found from the address of the area SD is not greater than the permissible band interval, or after the step 434 has ended, the processing flow shifts to a step 435. Here, whether the check of the band intervals in the whole area in the Y-axial direction is over or not is determined. When it is not over, the processing flow shifts to the step 432. By repeating the steps 432-434 in this manner, the band interval check for the whole area in the Y-axial direction is executed, whereupon the processing of FIG. 3E ends.

In this manner, at the step 400, the base data items of the area SD within the RAM 15 are examined on the basis of the band interval characteristic known beforehand, so as to erase the base data detected erroneously and to compensate for the base data failing to be detected.

That is, the band interval of the adjacent bands is compared with the minimum band interval $D_{min}$, and the base data of the band determined as being noise is erased from the area SD of the memory 15. Besides, the band interval of the adjacent bands is compared with the reference band interval corresponding to the band position, and the band left undetected is re-detected to correct the band position. Therefore, failure in the band detection attributed to a thin band or a close band interval can be prevented from occurring, and band arrayal data including no error can be obtained.

Thereafter, at the step 500, the base data items stored in the area SD of the memory 15 are read out in the order of the addresses corresponding to the Y-axial direction, so as to be stored in the disk device 16 and to be transmitted from the external interface circuit 17 to the external computer (not shown).

Here, among the detected base data items, ones corresponding to the analytical spectra in FIG. 6D are shown in FIG. 6E.

Although, in the foregoing embodiment, the reading of the band arrayal information of the bases of the gene imaged with X-rays has been described by way of example, the invention is not restricted thereto, but band arrayal information in the chromatogram of amino acids etc. may also be read. Besides, bands being moved by electrophoresis or the like may also be directly detected by a fixed sensor.

As described above, according to the present invention, a band arrayal pattern can be automatically read.

With a method wherein histograms are obtained every predetermined section in the lengthwise direction of lanes (in a Y-axial direction) and wherein band positions are detected on the basis of the histograms, the band positions of the respective lanes can be accurately detected even when the lanes are meandering.

With an apparatus according to the present invention, histograms can be obtained in parallel with the collection of density data, so that processing can be made faster.

With a method wherein the arrayal order of bands is read after detected band positions have been normalized to positions on a single line in the lengthwise direction of lanes in accordance with the slopes of the respective bands, the arrayal order of the bands can be accurately detected even when the bands incline in the individual lanes.

Further, with a method wherein the band interval of adjacent bands on the single line is compared with the minimum band interval as predetermined and a reference band interval according to a position on the single line and wherein the band is erased or re-detected, the erroneous reading of the band position can be prevented.

What is claimed is:

1. A method of automatically reading a band arrayal pattern having a plurality of bands in patterns arrayed substantially in a first direction and within a plurality of lanes extending substantially in a second direction perpendicular to the first direction, said method comprising the steps of:
   photoelectrically scanning the pattern to generate density data items made up of pixels;
   detecting histograms from the generated density data items, said histograms consisting of sums of the density data items of the pixels in a plurality of straight lines in said second direction;
   detecting from said histograms representative points for respective lanes, the points representing positions of said respective lanes in said first direction;
   detecting for said respective lanes density data trains of the pixels in straight lines in said second direction and passing the detected representative points; and
   detecting positions of the plurality of bands within said respective lanes in said second direction from the detected density data trains.

2. A method of automatically reading a band arrayal pattern as defined in claim 1, wherein the generating of the histograms and the detecting of the representative points are performed for each of a plurality of sections which are obtained by dividing said respective lanes in said second direction.

3. A method of automatically reading a band arrayal pattern as defined in claim 1, wherein said representative points are points which represent central positions of said respective lanes in said first direction.

4. A method of automatically reading a band arrayal pattern as defined in claim 1, wherein;
the generating of the representative points generates a plurality of points which represent a plurality of positions in each lane in said first direction;
the detection of the histograms detects for said each lane a plurality of density data trains consisting of density data trains of the pixels in a plurality of straight lines in said second direction which pass said plurality of representative points respectively; and
the detection of the band positions detects positions of a plurality of bands in said second direction on the basis of each of said plurality of density data trains for said each lane and detects a plurality of band positions for the respective bands within said each lane from the plurality of representative point positions detected and the plurality of band positions detected for each of said plurality of density data trains.

5. A method of automatically reading a band arrayal pattern as defined in claim 4, wherein said plurality in representative points of said each lane are a point which represents a central position of said each lane and points which represent positions of both peripheral edge parts of said each lane.

6. A method of automatically reading a band arrayal pattern as defined in claim 5, wherein the detection of said plurality of representative points of said each lane is performed for each of a plurality of sections which are obtained by dividing said respective lanes in said second direction.

7. A method of automatically reading a band arrayal pattern as defined in claim 5, wherein the detection of the central position of said each lane and the positions of both peripheral edges parts of said each lane is such that the histograms for the plurality of lanes are differentiated to obtain differential curves, to detect a plus maximum value and a minus maximum value in said differential curves for said plurality of lanes, and to calculate a plus threshold value and a minus threshold value respectively having fixed relations to said plus maximum value and said minus maximum value, whereupon points respectively having said plus threshold value and said minus threshold value in the differential curve of the histogram of said each lane are detected as points which represent the positions of both said peripheral edge parts of said each lane, while a middle point of the representative points of said positions of said both peripheral edge parts is detected as a point which represents the central position of said each lane.

8. A method of automatically reading a band arrayal pattern as defined in claim 1 wherein the detection of a plurality of band positions based on density data trains detects pixel positions having maximum density data items in said density data trains.

9. A method of automatically reading a band arrayal pattern as defined in claim 1, wherein band positions detected along said second direction are normalized to positions on a single line in said second direction of said each lane in accordance with slopes of respectively corresponding bands.

10. A method of automatically reading a band arrayal pattern as defined in claim 9, further comprising, when a band interval of the adjacent bands at the band positions respectively normalized on said single line in said second direction is smaller than a minimum band interval of a predetermined value, interpreting one of said adjacent bands as noise and eliminating said one band, and, when said band interval of said adjacent bands is sufficiently greater than a reference band interval having a value corresponding to a position on said single line, re-detecting a band which ought to exist between said adjacent bands.

11. A method of automatically reading a band arrayal pattern as defined in claim 1, wherein the band arrayal pattern is a base band arrayal pattern of a gene.

12. An apparatus for automatically reading a band arrayal pattern having a plurality of band patterns arrayed substantially in a first direction within a plurality of lanes extending substantially in a second direction perpendicular to the first direction, said apparatus comprising:
photoelectric conversion means for photoelectrically converting the band arrayal pattern to generate density data items of respective pixels, said photoelectric conversion means including means for photoelectrically converting a predetermined number of pixels in a straight line in said first direction and means for changing the position of the straight line in said second direction;
a first memory having a like predetermined number of storage locations for storage of data;
addition means for adding the density data items of said predetermined number of pixels and data within one storage location of said first memory and writing the result of such addition into said first memory in synchronism with the photoelectric conversion of said predetermined number of pixels in the straight line in said first direction by said photoelectric conversion means, thereby to form in said first memory histograms which are sums of the density data items of the pixels in a plurality of straight lines in said second direction respectively;
a second memory for storing said density data items of said pixels in succession in synchronism with the photoelectric conversion of said pixels by said photoelectric conversion means; and
processing means for detecting a point representative of a position in each lane in said first direction from the histogram within said first memory and, for the respective lanes, reading out from said second memory a density data train for the pixels in the straight line in said second direction passing the detected representative points, and for detecting positions of the respective bands within said each lane in said second direction from said density data trains read out from said second memory.

13. An apparatus for automatically reading a band arrayal pattern as defined in claim 12, wherein:
said second memory includes first and second areas, each holding a set of the density data items of the pixels within one of a plurality of sections of the pixels juxtaposed in said second direction by said photoelectric conversion means, and means for writing the sets of the density data items within the plurality of sections of the pixels alternatively into the first and second areas in synchronism with the delivery of sections of the density data items of the respective sections of the pixels by said photoelectric conversion means, said first memory includes means for resetting said first memory in synchronism with the delivery of the sets of the density data items of said respective sections of the pixels by said photoelectric conversion means, whereby said first memory holds the histograms concerning the density data items of the plurality of pixels within one of said sections of the pixels, and said processing means is means for detecting the position of a point representative of a position of said each lane within said each section of the pixel in synchronism with the delivery of the sets of the density data items of the respective sections of the pixels by said photoelectric conversion means, for detecting positions of a pixel train lying in a line which connects a first point representative of the position of said each lane within the detected one of the sections of the pixels and a second point representative of the position of said each lane of the section of the pixels directly preceding said one section of the pixels previously detected, for reading out the density data items for the pixels at the detected positions from said first and second areas of said second memory, and for detecting positions of the respective bands within the respective lanes in said second direction on the basis of density data trains read out from said second memory as to said plurality of sections of the pixels.

14. An apparatus for automatically reading a band arrayal pattern as defined in claim 13, wherein:

said first memory delivers the stored data items in succession in synchronism with the photoelectric conversion of the plurality of pixels on said straight line in said first direction by said photoelectric conversion means, and said addition means is means for successively receiving and adding the density data items for said plurality of pixels on said straight line in said first direction as delivered by said photoelectric conversion means and the data items read out from said first memory.

15. An apparatus for automatically reading a band arrayal pattern as defined in claim 12, wherein the band arrayal pattern is a base band arrayal pattern of a gene.

* * * * *